(12) United States Patent
Parr et al.

(10) Patent No.: US 9,713,693 B2
(45) Date of Patent: Jul. 25, 2017

(54) EXHAUST VALVE AND METHOD OF MANUFACTURE THEREFORE

(75) Inventors: William Edgar Parr, Ledgewood, NJ (US); Joseph Guzman, Yonkers, NY (US); Eric Andrew Lieberman, Scotch Plains, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1011 days.

(21) Appl. No.: 13/636,193

(22) PCT Filed: Mar. 15, 2011

(86) PCT No.: PCT/IB2011/051085
§ 371 (c)(1),
(2), (4) Date: Sep. 20, 2012

(87) PCT Pub. No.: WO2011/121472
PCT Pub. Date: Oct. 6, 2011

(65) Prior Publication Data
US 2013/0118499 A1     May 16, 2013

Related U.S. Application Data

(60) Provisional application No. 61/318,562, filed on Mar. 29, 2010.

(51) Int. Cl.
*A61M 16/20* (2006.01)
*A61M 16/06* (2006.01)
*A62B 18/10* (2006.01)
*F16K 15/16* (2006.01)
*A61M 16/00* (2006.01)
*B23P 15/00* (2006.01)

(52) U.S. Cl.
CPC ........ *A61M 16/20* (2013.01); *A61M 16/0057* (2013.01); *A61M 16/06* (2013.01); *A61M 16/208* (2013.01); *A62B 18/10* (2013.01); *B23P 15/001* (2013.01); *F16K 15/16* (2013.01); *Y10T 29/49412* (2015.01)

(58) Field of Classification Search
CPC .... A61M 16/06; A61M 16/20; A61M 16/208; B23P 15/001
See application file for complete search history.

(56) References Cited

U.S. PATENT DOCUMENTS 4,508,139 A * 4/1985 Teumer ................. F16K 15/033
137/315.13
5,295,478 A    3/1994   Baldwin
5,645,049 A    7/1997   Foley et al.
(Continued)

FOREIGN PATENT DOCUMENTS

EP          1854493 A2    11/2007
WO       02089889 A1    11/2002

*Primary Examiner* — Justine Yu
*Assistant Examiner* — Timothy Stanis
(74) *Attorney, Agent, or Firm* — Michael W. Haas (57) ABSTRACT

A valve (20) is provided that selectively controls flows of fluid through a valve opening (50). The valve (20) includes an elastically resilient valve member (54) that is seated in a member pocket (52) with a valve flap (76) that covers the valve opening (50). The valve flap (76) substantially prevents flows of fluid in one direction through the valve opening (50), but permits flows of fluid in the other direction.

15 Claims, 5 Drawing Sheets

(56) References Cited

U.S. PATENT DOCUMENTS

| | | | |
|---|---|---|---|
| 2004/0250863 A1* | 12/2004 | Atkeson | F16K 15/031 137/855 |
| 2004/0261795 A1 | 12/2004 | Brunell | |
| 2009/0065729 A1* | 3/2009 | Worboys | A61M 16/06 251/367 |
| 2009/0194100 A1* | 8/2009 | Minagi | A61F 5/08 128/200.24 |
| 2010/0258133 A1* | 10/2010 | Todd | A61M 16/1065 128/207.12 |
| 2012/0204333 A1* | 8/2012 | Serin | E03C 1/1225 4/211 |
| 2012/0304985 A1* | 12/2012 | Lalonde | A61M 16/06 128/201.13 |

\* cited by examiner

EXHAUST VALVE AND METHOD OF MANUFACTURE THEREFORE

FIELD OF THE INVENTION

The invention relates to an exhaust valve installed in a respiration therapy mask, and a method of manufacture therefore.

BACKGROUND

Exhaust valves implementing a flap to regulate flows of fluid through an opening are known. However, particularly within respiration therapy equipment, such valves typically require mechanism for holding the flap securely in place during use that are relatively costly. For example, such valves may require one or more of ultrasonic welding, snap-fitting retainer pieces, expensive adhesives, intricate assembly techniques, and/or other costly mechanisms for holding a valve flap in place.

SUMMARY

One aspect of the invention relates to a valve configured to control flows of fluid through the valve. In one embodiment, the valve comprises a valve opening, a member pocket, a first protrusion, a second protrusion, and a valve member. The valve opening is formed in a first wall, wherein the first wall separates a first body of fluid on a first side of the first wall from a second body of fluid on a second side of the first wall. The member pocket is formed through a second wall that runs transverse to the first wall. The member pocket passes through the second wall from a front opening in the side of the second wall facing toward the valve opening to a rear opening on a side of the second wall opposite the valve opening. A cross sectional area of the front opening is smaller than a cross sectional area of the rear opening. The first protrusion is formed at or near an edge of the front opening of the member pocket, and protrudes inwardly into the member pocket from an edge of the front opening closest to the valve opening toward the rear opening. The first protrusion is shaped to form a cavity between the first protrusion and the inner surface of the member pocket. The second protrusion is formed at or near an edge of the front opening of the member pocket opposite the first protrusion, and protrudes from the inner surface of the member pocket toward the first protrusion. The valve member is formed substantially wholly from a flexibly resilient material. The valve member comprises a member body and a valve flap. The member body is configured to be seated within the member pocket, and includes a wedge and a slot. The wedge is configured to rest in the cavity between the first protrusion and the inner surface of the member pocket. The slot is configured to receive the second protrusion therein such that the seating of the wedge in the cavity and the reception of the second protrusion into the slot hold the member body in place within the member pocket. The valve flap extends from the member body to cover the valve opening on the first side of the valve opening such that flows of fluid from the first body of fluid to the second body of fluid are substantially prevented by the valve flap. The valve flap is configured to resiliently flex away from the valve opening to permit flows of fluid from the second body of fluid to the first body of fluid.

Another aspect of the invention relates to a method of manufacturing a valve configured to control flows of fluid through the valve. In one embodiment, the method comprises forming a first wall with a valve opening therein, wherein the first wall separates a first body of fluid on a first side of the first wall from a second body of fluid on a second side of the first wall; forming a second wall with a member pocket therein, wherein the second wall at the member pocket runs transverse to the first wall at the valve opening, wherein the member pocket passes through the second wall from a front opening in the side of the second wall facing toward the valve opening to a rear opening on a side of the second wall opposite the valve opening, wherein a cross sectional area of the front opening is smaller than a cross sectional area of the rear opening; forming a first protrusion at or near an edge of the front opening of the member pocket, the first protrusion protruding inwardly into the member pocket from an edge of the front opening closest to the valve opening toward the rear opening, the first protrusion being shaped to form a cavity between the first protrusion and the inner surface of the member pocket; forming a second protrusion at or near an edge of the front opening of the member pocket opposite the first protrusion, wherein the second protrusion protrudes from the inner surface of the member pocket toward the first protrusion; and inserting a valve member into the member pocket through the rear opening to seat the valve member in the member pocket. The valve member comprises a member body and a valve flap. The member body is configured to be seated within the member pocket, and includes a wedge and a slot. The wedge is configured to rest in the cavity between the first protrusion and the inner surface of the member pocket. The slot is configured to receive the second protrusion therein such that the seating of the wedge in the cavity and the reception of the second protrusion into the slot hold the member body in place within the member pocket. The valve flap extends from the member body to cover the valve opening on the first side of the valve opening such that flows of fluid from the first body of fluid to the second body of fluid are substantially prevented by the valve flap. The valve flap is configured to resiliently flex away from the valve opening to permit flows of fluid from the second body of fluid to the first body of fluid.

Yet another aspect of the invention relates to a valve configured to control flows of fluid through the valve. In one embodiment the valve comprises means for communicating a first body of fluid with a second body of fluid, the means for communicating being formed in a first wall, wherein the first wall separates the first body of fluid on a first side of the first wall from the second body of fluid on a second side of the first wall; means for holding a valve member, the means for holding being formed through a second wall, wherein the second wall at the means for holding runs transverse to the first wall at the means for communicating; means for seating a valve member formed by a first protrusion at or near an edge of the front opening of the member pocket and an inner surface of the means for holding, the first protrusion protruding inwardly into the means for holding away from the means for communicating; means for retaining a valve member formed at or near an edge of the means for holding facing toward the means for communicating, wherein the means for retaining protrudes from the inner surface of the means for holding toward the means for seating; and a valve member formed substantially wholly from a flexibly resilient material. The valve member comprises body means for resting within the means for holding, the body means comprising a wedge and a slot, the wedge being configured to rest in the means for seating, the slot being configured to receive the means for retaining therein such that the seating of the wedge in the means for seating and the reception of the means for retaining into the slot hold the body means in place within the means for holding; and means for controlling flows of fluid between the first body of fluid and the second body of fluid through the means for communicating such that flows of fluid from the first body of fluid to the second body of fluid are substantially prevented by the means for controlling flows of fluid, wherein the means for controlling flows of fluid is configured to selectively permit flows of fluid from the second body of fluid to the first body of fluid.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
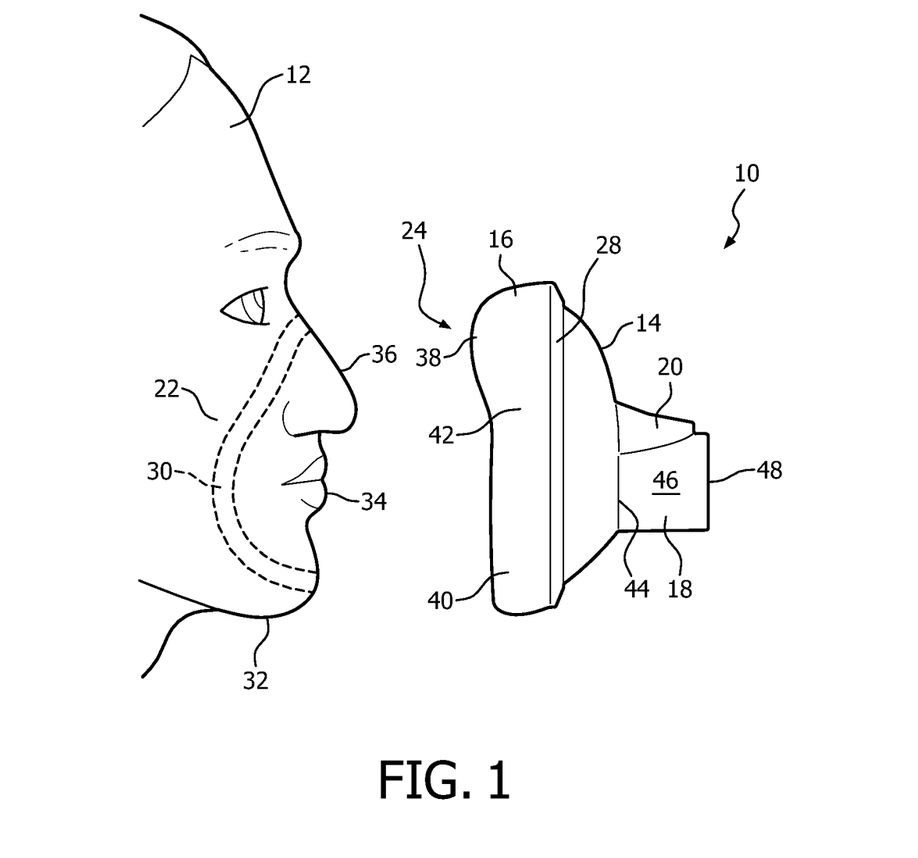
FIG. 1 illustrates a mask for use in therapeutic gas delivery to one or more external orifices of a subject, according to one or more embodiments of the invention.

FIG. 1 illustrates a mask 10 for use in therapeutic gas delivery to one or more external orifices (e.g., the nostrils and/or mouth) of a subject 12 in accordance with an embodiment of the present invention. The mask 10 may generally include a mask body 14, a seal portion 16, a source connector 18, and an exhaust valve 20. The mask 10 is configured to be placed against the face 22 of subject 12 with a substantially sealed interface there between such that a chamber 24 is formed by mask 10 and the face of subject 12 that encloses the one or more external orifices of subject 12. During use, a breathable substance can be provided into chamber 24 from a source (not shown) of the breathable substance through source connector 18.

Mask body 14, in one embodiment, is made of a relatively more rigid material (higher durometer material) than seal portion 16. For example, mask body 14 may be made from polycarbonate, or other suitable material. The mask body 14 provides structural rigidity to the mask 10 and, in some embodiments, may be a portion of a disposable mask that is retained when replacing the seal portion 16. The mask body 14/seal portion 16 may be formed by a two-step molding or assembly process. For example, the relatively harder mask body 14 may be molded first and then inserted into a second mold for the seal portion 16, which is injection molded to form around and/or into the mask body 14. In one embodiment, mask body 14 and seal portion 16 are of a similar durometer (e.g., less rigid), and/or may be formed as a single piece.

Seal portion 16 may be made of a relatively soft and/or flexible material so that the seal portion 16 conforms to the shape of the face 22 of subject 12 when held against it. Seal portion 16 may be made of, for example, silicone or an elastomeric material. In one embodiment, seal portion 16 has an arcuate or partially tubular cross-sectional configuration (also referred to as a concavo-convex cross-section, having a generally concave inner surface and generally convex outer surface). In one embodiment, seal portion 16 has a generally rounded, convex face engaging surface for engaging face 22 of subject 12. In one embodiment, the face engaging surface has a more flattened, convex configuration. Also, different regions of seal portion 16 around the perimeter of mask body 14 may have different cross-sectional configurations. Various other seal portion configurations will become apparent to those skilled in the art.

In one embodiment, seal portion 16 is attached to mask body 14 at an attachment region 28, as shown in FIG. 1. Attachment region 28 may be along the perimeter or edge of the mask body 14 and along a perimeter or edge of the seal portion 16, such that there is some overlap of the respective edges of the mask body 14 and the seal portion 16, as shown. Accordingly, there is some material of the mask body 14 that engages with some material of seal portion 16, such that a layered connection is formed. Other embodiments are contemplated in which there is no overlap, such as by attaching mask body 14 and seal portion 16 with their edges end to end (e.g., by an adhesive connection), and/or where mask body 14 and seal portion 16 are formed as a single piece.

In one embodiment, mask body 14 and seal portion 16 are configured to engage face 22 of subject 12 in an engagement region 30 that extends from between the chin 32 and lips 34, upwardly along region 30 on opposite sides of the mouth of subject 12, and across the nose 36 and over the bridge of the nose 36, as shown. In this embodiment, seal portion 16 is generally oblong or pear shaped, as shown in FIG. 1. Seal portion 16 accordingly includes an upper portion 38, a lower portion 40, and a transition portion 42. Upper portion 38, which may be configured to engage the face 22 of subject 12 across the bridge of the nose 36, has a radius of curvature that is relatively smaller than the radius of curvature R2 of lower portion 40. Lower portion 40, with its comparatively larger radius of curvature, may be configured to engage the face 22 of subject 12 between chin 32 and lips 34. Transition portion 42 extends generally from upper portion 38 to lower portion 40 and engages the face 22 of subject 12 and beneath the eyes. To facilitate creating a sealed engagement with face 22 of subject 12, transition portion 42 of seal portion 16 has more material in its cross-section, and has a greater linear length (i.e., if seal portion 16 were to be unrolled or straightened into a linear configuration) when measured in a direction extending orthogonally away from mask body 14, than each of upper portion 38 and lower portion 40, so as to effectively block fluid within chamber 24 from reaching the eyes of subject 12.

While the embodiment of seal portion 16 and mask body 14 may be sized to enclose the mouth and nose 36 of subject, this is not intended to be limiting. In one embodiment, mask 10 may be configured to enclose fewer external orifices of the airway of subject 12 (e.g., only the nostrils, only one nostril, only the mouth, etc.). One of ordinary skill in the art will appreciate that the configuration of mask 10 may vary and is not limited to a particular size or configuration, as subject 12 may range in age, size, and/or medical treatment required so as to require appropriate selection from among a variety of different mask sizes and configurations.

On a side of the mask body 14 that is opposite from seal portion 16, mask body 14 forms an opening 44 for receipt of source connector 18. Through opening 44, a breathable substance is provided into chamber 24 for inhalation by subject 12. In one embodiment, opening 44 is configured to connect with source connector 18.

In one embodiment, source connector 18 comprises a conduit 46 that forms a fluid flow path, when connected with mask body 14, from opening 44 to a source interface opening 48 formed in source connector 18. Source connector 18 is configured to connect a source of a breathable substance to the fluid flow path between opening 44 of mask body 14 and source interface opening 48 so that the breathable substance can be delivered from source interface opening 48 to chamber 24 for inhalation by subject 12. Source connector 18 may be formed integrally with mask body 14, or source connector may be formed separately from mask body 14 and then coupled to mask body 14. The connection between source connector 18 and mask body may be permanent (or substantially so), or selectively removable. For example, source connector 18 may be securely attached to opening 44 formed in mask body 14 by a permanent snap fit, an adhesive, heat staking, ultra-sonic welding, and/or otherwise secured to mask body 14. In one embodiment, source connector 18 is formed from a relatively rigid material (e.g., rigid silicone resin, Polycarbonate, Polyethylene Terepthalate Glycol, Polyethylene Terepthalate, Polypropylene, etc.).

In one embodiment, source connector 18 is configured to selectably and releasably engage the source of the breathable substance. In one embodiment, source connector 18 is configured to be permanently attached to the source and/or to be formed integrally with the source. The source of the breathable substance may include one or more of metered dose inhaler, a pressurized metered dose inhaler, a static chamber in communication with an inhaler, a nebulizer, a spacer, an aerosol dispenser, and/or other suitable sources of breathable substances. It will be appreciated that, in order to appropriately interface with mask body 14 and the source of the breathable substance, source connector 18 can be of various sizes, shapes, and configurations other than the ones illustrated in FIG. 1.

Exhaust valve 20 is configured to selectively exhaust gas exhaled from the enclosed one or more external orifices of subject 12 to ambient atmosphere. However, exhaust valve 20 is further configured to substantially seal the fluid flow path formed within source connector 18 from inflows of ambient atmosphere. As such, exhaust valve 20 is a one-way valve.

Figure 2:
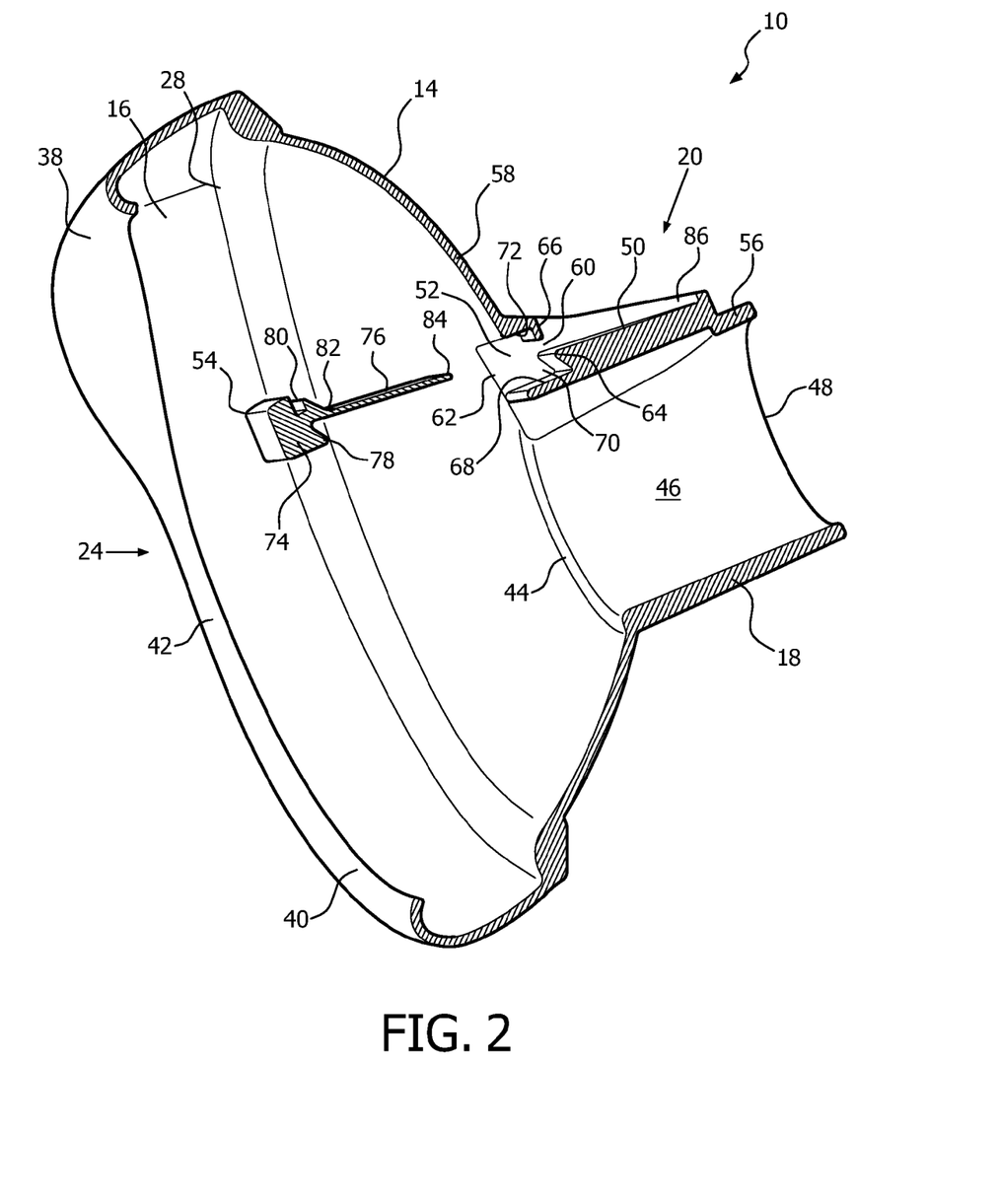
FIG. 2 illustrates a sectional view of a mask for use in therapeutic gas delivery to one or more external orifices of a subject including an exhaust valve that is exploded, in accordance with one or more embodiments of the invention.
Figure 3:
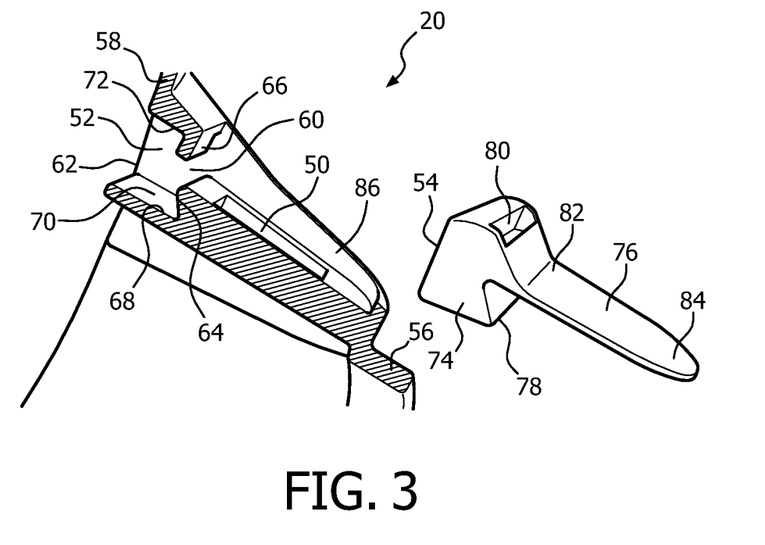
FIG. 3 illustrates an exploded view of an exhaust valve, according to one or more embodiments of the invention.
Figure 4:
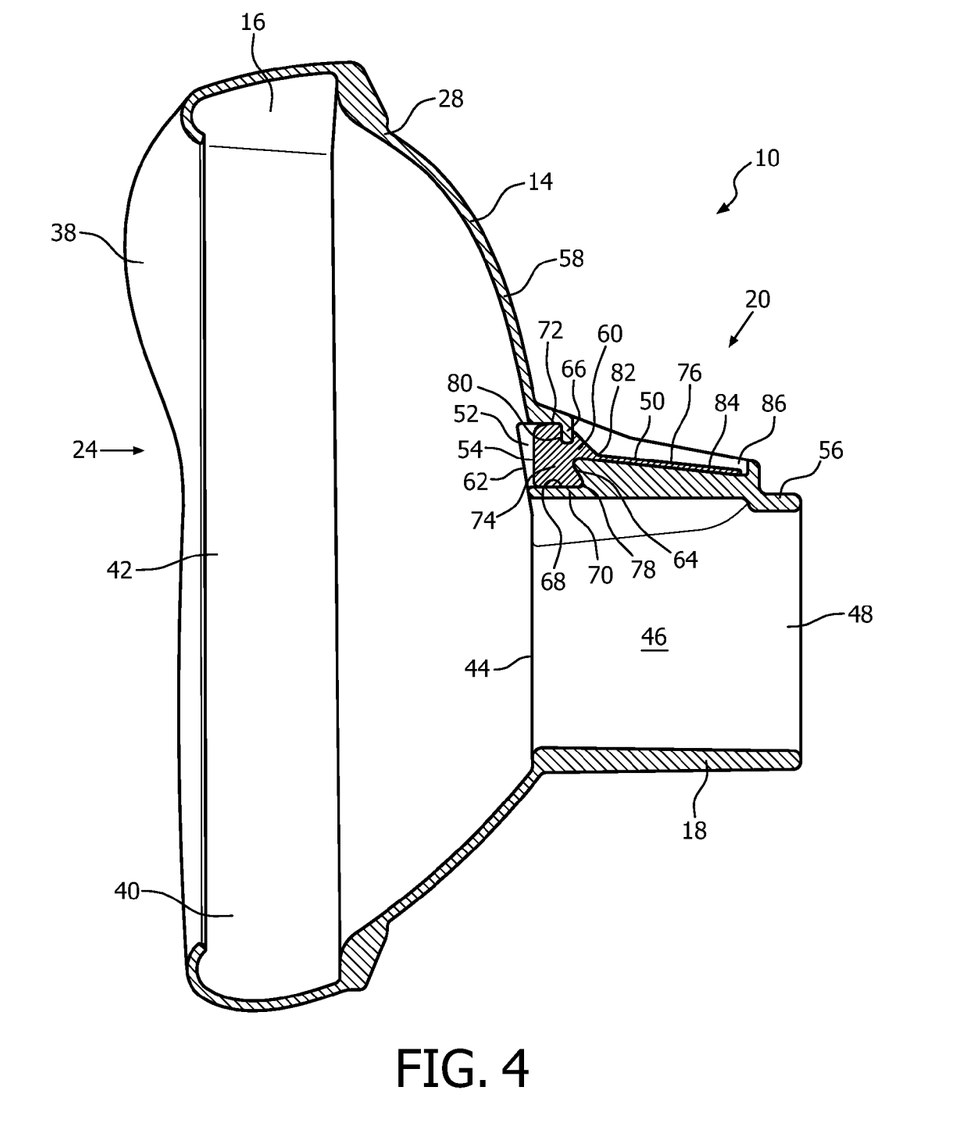
FIG. 4 illustrates a sectional view of a mask for use in therapeutic gas delivery to one or more external orifices of a subject including an exhaust valve that is assembled, in accordance with one or more embodiments of the invention.

FIGS. 2-4 illustrate sectional views of mask 10 that shows the configuration of exhaust valve 20. FIGS. 2 and 3 show an exploded view of exhaust valve 20 (FIG. 3 is magnified), and FIG. 4 illustrates exhaust valve 20 fully assembled. As can be seen in FIGS. 2-4, exhaust valve 20 includes one or more valve openings 50, a member pocket 52, and a valve member 54.

The valve opening 50 is formed in a wall 56 of source connector 18 on the top of source connector 18 if mask 10 is applied to the face of a subject (e.g., subject 12 in FIG. 1), and the face of the subject is being held upright. Hereinafter, references to "top", and "bottom" refer to relative locations when mask 10 has this general orientation. The wall 56 separates a first body of fluid (e.g., ambient atmosphere) on a first side of wall 56 from a second body of fluid (e.g., fluid within conduit 46) on a second side of wall 56. The valve opening 50 provides a pathway through which the first body of fluid and the second body of fluid are placed in fluid communication.

The member pocket 52 is configured to hold valve member 54 in place. The member pocket 52 is formed through a wall 58 of mask body 14. The wall 58 runs transverse to wall 56 at valve opening 50. Although in FIGS. 2-4 wall 56 and wall 58 are formed as discrete physical structures separated by a junction, this is not intended to be limiting. The wall 56 and the wall 58 may be formed as a single structure that arcs or slopes away from valve opening 50 to provide wall 58 at an angle to wall 56. Further, although in mask 10 wall 58 is a structure that has a function other than providing a housing for member pocket 52 (e.g., mask body 14 seals one or more external airway orifices of the subject from ambient atmosphere; see FIG. 1), this will not be viewed as limiting. In one embodiment, wall 58 is formed with the sole purpose of providing a housing for member pocket 52.

As can be seen in FIGS. 2-4, member pocket 52 passes through wall 58 from a front opening 60 in the side of wall 58 facing valve opening 50 to a rear opening 62 on a side of wall 58 opposite valve opening 50. The cross sectional area of front opening 60 is smaller than rear opening 62 by virtue of physical features formed within member pocket 52 to retain valve member 54 therein. These physical features include a lip 64 and a cleat 66.

The lip 64 is formed at or near an edge of front opening 60. The portion of the edge of front opening 60 on which lip 64 is formed is the portion of the edge that is closest to valve opening 50 (e.g., the "bottom" edge). The lip 64 is formed to protrude inwardly into member pocket 52 from the edge of front opening 60 toward rear opening 62. The lip 64 is formed such that a side of lip 64 opposite the front opening 60 cooperates with an inner surface 68 of member pocket 52 to form a cavity 70. In one embodiment, the side of lip 64 that forms cavity 70 with inner surface 68 is straight, as is inner surface 68, such that cavity 70 is wedge shaped. This is not intended to be limiting. The side of lip 64 and/or inner surface 68 may be rounded, include one or more protrusions, slots, and/or other features.

The cleat 66 is a protrusion formed at or near the edge of front opening 60. The portion of the edge of front opening 60 at which cleat 66 is formed in FIGS. 2-4 is opposite lip 64 (e.g., at the "top" of the edge). The cleat 66 protrudes from an inner surface 72 of into front opening 60. In the configuration of cleat 66 and lip 64 shown in FIGS. 2-4 with cleat 66 opposite from lip 64, cleat 66 protrudes from the edge of front opening 60 toward lip 64.

As was mentioned above, in one embodiment, the components of mask 10 that include member pocket 52, lip 64 and cleat 66 (e.g., mask body 14 and/or source connector 18) are formed from a rigid material. In one embodiment, the portions of mask 10 that include member pocket 52, lip 64 and cleat 66 are formed from a resiliently flexible material. In this embodiment, one or both of lip 64 and/or cleat 66 are formed from a rigid material separate from the resiliently flexible component within which they are disposed. The rigidity of lip 64 and/or cleat 66 may operate to hold valve member 54 more securely within member pocket 52. By way of non-limiting example, lip 64 and/or cleat 66 may be formed from rigid silicone resin, Polypropylene, Polycarbonate, Polyethylene Terepthalate Glycol, Polyethylene Terepthalate, and/or other rigid materials.

The valve member 54 is configured to be held within member pocket 52, and to control flows of fluid through valve opening 50 between the first body of fluid and the second body of fluid. In one embodiment, valve member 54 includes a member body 74, a valve flap 76, and/or other components.

The member body 74 has a shape that generally conforms to the shape of member pocket 52. As such, among other physical features, member body 74 includes a wedge 78 and a slot 80. The wedge 78 is formed at a corner of member body 74 that faces towards valve opening 50 when exhaust valve 20 is assembled, and is toward the "bottom" of member body 74. The wedge 78 is a protrusion or other physical feature of member body 74 with a shape that corresponds to cavity 70 such that when wedge 78 member body 74 is seated within member pocket 52, lip 64 is disposed between wedge 78 and valve flap 76. The slot 80 is an intrusion into member body 74. In the embodiment shown in FIGS. 2-4, slot 80 is formed at a corner of member body 74 that faces towards valve opening 50 when exhaust valve 20 is assembled, and is toward the "top" of member body 74. The shape of slot 80 corresponds to the shape of cleat 66 such that when member body 74 is seated within member pocket 52, cleat 66 is received into slot 80.

The valve flap 76 extends from member body 74 from a proximal end 82 to a distal end 84. The valve flap 76 attaches to member body 74 between lip 64 and cleat 66 on the side of member body 74 that faces valve opening 50. As such, when member body 74 is installed in exhaust valve 20, valve flap 76 extends out of member pocket 52 through front opening 60. The valve flap 76 is shaped to cover valve opening 50 when valve member 54 is installed in exhaust valve 20. In one embodiment, a flap seat 86 is formed in wall 56 about valve opening 50 to provide a seat for valve flap 76.

The valve flap 76 is configured to cover valve opening 50 on the first side of valve opening 50 such that flows of fluid from the first body of fluid to the second body of fluid are substantially prevented by valve flap 76. The valve flap 76 is formed from a resiliently elastic material such that responsive to a pressure differential between the second body of fluid and the first body of fluid breaching a threshold, the pressure of the second body of fluid causes valve flap 76 to resiliently flex away from valve opening 50, thereby permitting the flow of fluid from the second body of fluid to the first body of fluid. However, if the pressure differential between the second body of fluid and the first body of fluid does not breach the threshold, then valve flap 76 remains in place over valve opening 50.

In one embodiment, all of valve member 54 is formed from one or more resiliently elastic materials. For example, valve member 54 may be formed from silicone, thermal plastic elastomers, rubber, and/or other resiliently elastic materials. The one or more materials may have a durometer of between about 20 and about 80.

During assembly of exhaust valve 20, valve member 54 is inserted through member pocket 52, valve flap 76 first, until valve member 54 is held securely in member pocket 52. This includes seating wedge 78 within cavity 70, and receiving cleat 66 into slot 80. This provides a simple (and/or cost effective) mechanism for installing valve member 54 in exhaust valve 20, while the seating of wedge 78 in cavity 70 and/or the reception of cleat 66 into slot 80 provides a secure hold on valve member 54 that will not become insecure during usage. The elasticity of valve member 54 may provide further security between the engagement, as the equilibrium dimensions of valve member 54 may cause compression of valve member 54 by member pocket 52 at one or more locations to further provide friction security for the seating of valve member 54 within member pocket 52. In one embodiment, the interaction between the physical feature of member pocket 52 and valve member 54 provide the only mechanism for securing valve member 54 within member pocket 52. In one embodiment, valve member 54 is further secured within member pocket 52 with one or more of adhesive, heat staking, ultra-sonic welding, a cover positioned to close rear opening 62, and/or other mechanisms for securing valve member 54 within member pocket 52.

By virtue of the engagement between wedge 78 and cavity 70, and between slot 80 and cleat 66, valve member 54 is able to be secured within member pocket 52 in an embodiment in which valve member 54 is formed entirely from one or more elastically resilient materials and member pocket 52 (and lip 64 and cleat 66) is formed from one or more rigid materials. Further, the simple nature if the installment of valve member 54 into member pocket 52 provides an enhancement over conventional valves which require more complicated assembly techniques and/or more costly materials.

It will be appreciated that the description of exhaust valve 20 in the context of mask 10 is not intended to be limiting. The principles described above could be applied to a valve disposed in other therapeutic respiratory equipment. For example, exhaust valve 20 could be disposed within a spacer chamber, a conduit between a pressure support device and a subject interface appliance, nebulizers, nebulizer mouth pieces, medical compressors, and/or other therapeutic respiratory equipment. Further, exhaust valve 20 could be included within other types of systems to control flows of fluids between two separate bodies of fluids within and/or outside of the medical device arts.

Although exhaust valve 20 is shown and described with including at least portions that are incorporated integrally into the walls of components of mask 10, this is not limiting. In one embodiment, exhaust valve 20 may be manufactured and assembled wholly separate from a system in which it is going to be installed (e.g., mask 10) and then installed after manufacture. For example, valve opening 50 and member pocket 52 could be formed separately from wall 56 and wall 58, and then exhaust valve 20 could be installed in wall 56 and/or wall 58 in tact.

Figure 5:
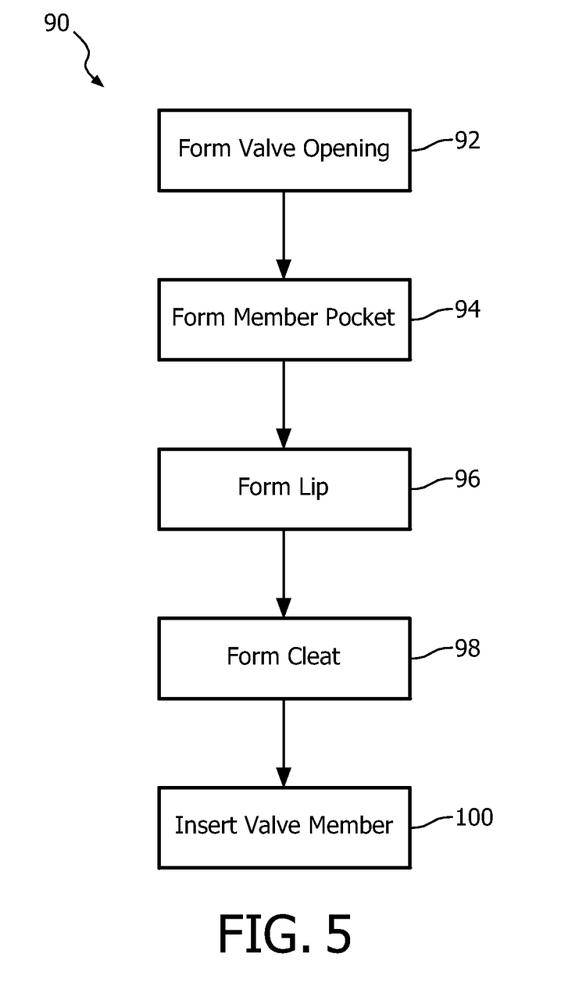
FIG. 5 illustrates a method of manufacturing a valve, according to one or more embodiments of the invention.

FIG. 5 illustrates a method 90 of manufacturing a valve configured to control flows of fluid through the valve. The operations of method 90 presented below are intended to be illustrative. In some embodiments, method 90 may be accomplished with one or more additional operations not described, and/or without one or more of the operations discussed. Additionally, the order in which the operations of method 90 are illustrated in FIG. 5 and described below is not intended to be limiting.

At an operation 92, a valve opening is formed in a first wall. The first wall separates a first body of fluid from a second body of fluid. In one embodiment, the first wall is the same as or similar to wall 56 (shown in FIGS. 1-4 and described above). In one embodiment, the valve opening is similar to or the same as valve opening 50 (shown in FIGS. 1-4 and described above).

At an operation 94, a member pocket is formed in a second wall. The second wall runs transverse to the first wall at the valve opening. The member pocket passes through the second wall from a front opening in the side of the second wall facing toward the valve opening to a rear opening on a side of the second wall opposite the valve opening. The cross sectional area of the front opening is smaller than the cross sectional area of the rear opening. In one embodiment, the member pocket is similar to or the same as member pocket 52 (shown in FIGS. 1-4 and described above).

At an operation 96, a lip is formed at or near an edge of the front opening of the member pocket. The lip protrudes inwardly into the member pocket from an edge of the front opening closes to the valve opening toward the rear opening. The lip is shaped to form a cavity between the lip and the inner surface of the member pocket. In one embodiment, the lip is similar to or the same as lip 64 (shown in FIGS. 2-4 and described above).

At an operation 98, a cleat is formed at or near an edge of the front opening of the member pocket opposite the lip. The cleat protrudes from the inner surface of the member pocket toward the lip. In one embodiment, the cleat is similar to or the same as cleat 66 (shown in FIGS. 2-4 and described above).

At an operation 100, a valve member is inserted into the member pocket through the rear opening of the member pocket until the valve member is seated in the member pocket. The valve member includes a member body and a valve flap. The member body includes a wedge and a slot. The wedge is configured to rest in the cavity formed by the lip and the inner surface of the member pocket. The slot is configured to receive the cleat therein. The valve flap of the valve member extends from the member body to cover the valve opening such that flows of fluid from the first body of fluid to the second body of fluid are substantially prevented by the valve flap. The valve flap is further configured, upon installation, to resiliently flex away from the valve opening to permit flows of fluid from the second body of fluid to the first body of fluid. In one embodiment, the valve member is similar to or the same as valve member 54 (shown in FIGS. 1-4 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A valve configured to exhaust flows of fluid through the valve to ambient atmosphere, the valve configured to be installed in a respiration therapy mask, the valve comprising:
    a valve opening formed in a first wall, wherein the first wall separates a first body of fluid on a first side of the first wall from a second body of fluid on a second side of the first wall, wherein the first body of fluid is ambient atmosphere;
    a member pocket formed through a second wall, wherein the second wall runs transverse to the first wall, wherein the member pocket passes through the second wall from a front opening in the side of the second wall facing toward the valve opening to a rear opening on a side of the second wall opposite the valve opening, wherein a cross sectional area of the front opening is smaller than a cross sectional area of the rear opening;
    a first protrusion formed at or near an edge of the front opening of the member pocket, the first protrusion protruding inwardly into the member pocket from an edge of the front opening closest to the valve opening toward the rear opening, the first protrusion being shaped to form a cavity between the first protrusion and the inner surface of the member pocket and having an angled frontmost face;
    a second protrusion formed at or near an edge of the front opening of the member pocket opposite the first protrusion, wherein the second protrusion protrudes from the inner surface of the member pocket toward the first protrusion; and
    a valve member formed substantially wholly from a flexibly resilient material, the valve member comprising:
    a member body configured to be seated within the member pocket, the member body comprising a wedge and a slot, the wedge being configured to rest in the cavity between the first protrusion and the inner surface of the member pocket and having an angled face configured to engage the angled face of the first protrusion, the slot being configured to receive the second protrusion therein such that the seating of the wedge in the cavity and the reception of the second protrusion into the slot hold the member body in place within the member pocket; and
    a valve flap that extends from the member body to cover the valve opening on the first side of the valve opening such that flows of fluid from ambient atmosphere to the second body of fluid are substantially prevented by the valve flap, wherein the valve flap is configured to resiliently flex away from the valve opening to permit flows of fluid from the second body of fluid to ambient atmosphere while the mask is being worn by a subject, wherein a portion of the member body disposed distally of the slot has an angled face, the angled face extending from a proximal end of the valve flap and angled towards the slot such that a distal cross section of the portion is smaller than a proximal cross section of the portion.

2. The valve of claim 1, wherein the first wall and the second wall are formed integrally with each other.

3. The valve of claim 1, wherein the first wall, the second wall, the first protrusion, and the second protrusion are formed from a rigid material.

4. The valve of claim 1, wherein the valve is configured to be assembled by inserting the valve member through the rear opening, valve flap first until the wedge is seated in the cavity and the second protrusion is received into the slot.

5. The valve of claim 1, wherein the valve flap is configured to permit flows of fluid from the second body of fluid to ambient atmosphere responsive to a pressure differential between ambient atmosphere and the second body of fluid that causes the valve flap to resiliently flex away from the valve opening.

6. A method of manufacturing a valve configured to exhaust flows of fluid through the valve ambient atmosphere, the valve configured to be installed in a respiration therapy mask, the method comprising:
    forming a first wall with a valve opening therein, wherein the first wall separates a first body of fluid on a first side of the first wall from a second body of fluid on a second side of the first wall, wherein the first body of fluid is ambient atmosphere;

forming a second wall with a member pocket therein, wherein the second wall at the member pocket runs transverse to the first wall at the valve opening, wherein the member pocket passes through the second wall from a front opening in the side of the second wall facing toward the valve opening to a rear opening on a side of the second wall opposite the valve opening, wherein a cross sectional area of the front opening is smaller than a cross sectional area of the rear opening;

forming a first protrusion at or near an edge of the front opening of the member pocket, the first protrusion protruding inwardly into the member pocket from an edge of the front opening closest to the valve opening toward the rear opening, the first protrusion being shaped to form a cavity between the first protrusion and the inner surface of the member pocket and having an angled frontmost face;

forming a second protrusion at or near an edge of the front opening of the member pocket opposite the first protrusion, wherein the second protrusion protrudes from the inner surface of the member pocket toward the first protrusion; and inserting a valve member into the member pocket through the rear opening to seat the valve member in the member pocket, wherein the valve member comprises:

a member body configured to be seated within the member pocket, the member body comprising a wedge and a slot, the wedge being configured to rest in the cavity between the first protrusion and the inner surface of the member pocket and having an angled face configured to engage the angled face of the first protrusion, the slot being configured to receive the second protrusion therein such that the seating of the wedge in the cavity and the reception of the second protrusion into the slot hold the member body in place within the member pocket; and a valve flap that extends from the member body to cover the valve opening on the first side of the valve opening such that flows of fluid from ambient atmosphere to the second body of fluid are substantially prevented by the valve flap, wherein the valve flap is configured to resiliently flex away from the valve opening to permit flows of fluid from the second body of fluid to ambient atmosphere while the mask is being worn by a subject, wherein a portion of the member body disposed distally of the slot has an angled face, the angled face extending from a proximal end of the valve flap and angled towards the slot such that a distal cross section of the portion is smaller than a proximal cross section of the portion.

7. The method of claim 6, wherein the first wall and the second wall are formed integrally with each other.

8. The valve of claim 6, wherein the first wall, the second wall, the first protrusion, and the second protrusion are formed from a rigid material.

9. The valve of claim 6, wherein inserting the valve member into the member pocket comprises inserting the valve member through the rear opening, valve flap first until the wedge is seated in the cavity and the second protrusion is received into the slot.

10. The method of claim 6, wherein the valve flap is configured to permit flows of fluid from the second body of fluid to ambient atmosphere responsive to a pressure differential between ambient atmosphere and the second body of fluid that causes the valve flap to resiliently flex away from the valve opening.

11. A valve configured to exhaust flows of fluid through the valve to ambient atmosphere, the valve configured to be installed in a respiration therapy mask, the valve comprising:

means for communicating ambient atmosphere and a second body of fluid with each other, the means for communicating being formed in a first wall, wherein the first wall separates ambient atmosphere on a first side of the first wall from the second body of fluid on a second side of the first wall;

means for holding a valve member, the means for holding being formed through a second wall, wherein the second wall at the means for holding runs transverse to the first wall at the means for communicating;

means for seating a valve member formed by a first protrusion at or near an edge of a front opening of a pocket portion of the means for holding and an inner surface of the means for holding, the first protrusion protruding inwardly into the means for holding away from the means for communicating and having an angled frontmost face;

means for retaining a valve member formed at or near an edge of the means for holding facing toward the means for communicating, wherein the means for retaining protrudes from the inner surface of the means for holding toward the means for seating; and a valve member formed substantially wholly from a flexibly resilient material, the valve member comprising:

body means for resting within the means for holding, the body means comprising a wedge and a slot, the wedge being configured to rest in the means for seating and having an angled face configured to engage the angled face of the first protrusion, the slot being configured to receive the means for retaining therein such that the seating of the wedge in the means for seating and the reception of the means for retaining into the slot hold the body means in place within the means for holding; and means for controlling flows of fluid between ambient atmosphere and the second body of fluid through the means for communicating such that flows of fluid from ambient atmosphere to the second body of fluid are substantially prevented by the means for controlling flows of fluid, wherein the means for controlling flows of fluid is configured to selectively permit flows of fluid from the second body of fluid to ambient atmosphere while the mask is being worn by a subject, wherein a portion of the body means disposed distally of the slot has an angled face, the angled face extending from a proximal end of the means for controlling flows of fluid and angled towards the slot such that a distal cross section of the portion is smaller than a proximal cross section of the portion.

12. The valve of claim 11, wherein the first wall and the second wall are formed integrally with each other.

13. The valve of claim 11, wherein the first wall, the second wall, the means for seating, and the means for retaining are formed from a rigid material.

14. The valve of claim 11, wherein the valve is configured to be assembled by inserting the valve member through the means for holding.

15. The valve of claim 11, wherein the means for controlling flows of fluid are configured to permit flows of fluid from the second body of fluid to ambient atmosphere responsive to a pressure differential between ambient atmosphere and the second body of fluid above a threshold pressure differential.

* * * * *